United States Patent
Woo et al.

(10) Patent No.: US 7,371,258 B2
(45) Date of Patent: May 13, 2008

(54) VALVED PROSTHESIS WITH POROUS SUBSTRATE

(75) Inventors: Yi-Ren Woo, Woodbury, MN (US); Abhay S. Pandit, Minneapolis, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 10/004,504

(22) Filed: Oct. 26, 2001

(65) Prior Publication Data

US 2003/0083741 A1 May 1, 2003

(51) Int. Cl.
*A61F 2/24* (2006.01)
(52) U.S. Cl. ............... 623/2.22; 623/2.2; 623/2.34
(58) Field of Classification Search ............ 623/2.2, 623/2.21, 2.22, 2.23, 2.24, 2.25, 2.26, 2.27, 623/2.28, 2.29, 2.3, 2.31, 2.32, 2.33
See application file for complete search history.

(56) References Cited

U.S. PATENT DOCUMENTS

| | | | |
|---|---|---|---|
| 3,685,059 A | | 8/1972 | Bokros et al. |
| 4,620,327 A | | 11/1986 | Caplan et al. |
| 4,648,881 A | | 3/1987 | Carpentier et al. |
| 4,798,611 A | | 1/1989 | Freeman, Jr. |
| 4,883,755 A | | 11/1989 | Carabasi et al. |
| 4,936,317 A | * | 6/1990 | MacGregor ............ 607/120 |
| 5,002,582 A | | 3/1991 | Guire et al. |
| 5,080,668 A | | 1/1992 | Bolz et al. |
| 5,147,400 A | | 9/1992 | Kaplan et al. |
| 5,147,514 A | | 9/1992 | Mechanic |
| 5,192,312 A | | 3/1993 | Orton |
| 5,194,596 A | | 3/1993 | Tischer et al. |
| 5,372,945 A | | 12/1994 | Alchas et al. |
| 5,578,075 A | * | 11/1996 | Dayton ............ 623/1.15 |
| 5,607,469 A | | 3/1997 | Frey |

(Continued)

FOREIGN PATENT DOCUMENTS

EP   0 271 216   6/1988

(Continued)

OTHER PUBLICATIONS

Belle et al., "Accelerated Endothelialization by Local Delivery of Recombinant Human Vascular Endothelial Growth Factor Reduces In-Stent Intimal Formation", Biochemical and Bio Physical Research Communication 235, 311-316 (1997).

(Continued)

*Primary Examiner*—Thomas J Sweet
(74) *Attorney, Agent, or Firm*—Hallie A. Finucane; Westman, Champlin & Kelly, P.A.

(57) ABSTRACT

An implantable prosthesis can be formed from an improved biocompatible material that provides for cellular colonization of the biocompatible material. Specifically, the biocompatible material is a rigid porous material. In embodiments of particular interest, the implantable prosthesis is a mechanical heart valve prosthesis with a rigid occluder. In some embodiments, the rigid occluder is formed from the biocompatible material. A filler comprising a hydrogel or a structural protein can be located within the pores. In some embodiments, a bioactive agent is within the pores. In some embodiments, the rigid occluder is formed from a polymer material, a carbonaceous solid or a ceramic material. The pores can extend through the rigid material.

37 Claims, 2 Drawing Sheets

U.S. PATENT DOCUMENTS

| | | | |
|---|---|---|---|
| 5,607,918 | A | 3/1997 | Eriksson et al. |
| 5,613,982 | A | 3/1997 | Goldstein |
| 5,628,781 | A | 5/1997 | Williams et al. |
| 5,649,906 | A * | 7/1997 | Gory et al. ............ 606/108 |
| 5,728,152 | A | 3/1998 | Mirsch, II et al. |
| 5,728,420 | A | 3/1998 | Keogh |
| 5,759,205 | A | 6/1998 | Valentini |
| 5,769,884 | A * | 6/1998 | Solovay ............... 623/1.13 |
| 5,811,151 | A | 9/1998 | Hendriks et al. |
| 5,817,327 | A | 10/1998 | Ducheyne et al. |
| 5,899,939 | A | 5/1999 | Boyce et al. |
| 6,013,106 | A | 1/2000 | Tweden et al. |
| 6,033,436 | A * | 3/2000 | Steinke et al. .......... 623/1.15 |
| 6,033,719 | A | 3/2000 | Keogh |
| 6,096,052 | A * | 8/2000 | Callister et al. ........ 606/157 |
| 6,099,561 | A * | 8/2000 | Alt ...................... 623/1.44 |
| 6,224,893 | B1 | 5/2001 | Langer et al. |
| 6,231,879 | B1 * | 5/2001 | Li et al. ................ 424/422 |
| 6,375,680 | B1 | 4/2002 | Carlyle |
| 6,432,116 | B1 * | 8/2002 | Callister et al. ........ 606/157 |
| 2002/0020417 | A1 * | 2/2002 | Nikolchev et al. ....... 128/831 |

FOREIGN PATENT DOCUMENTS

| | | |
|---|---|---|
| EP | 0 476 983 A1 | 9/1991 |
| EP | 0 506 477 A1 | 3/1992 |
| EP | 0 550 296 A2 | 11/1992 |
| EP | 0 616 814 A1 | 3/1994 |
| EP | 0 742 020 A2 | 1/1996 |
| EP | 1 064 958 | 1/2001 |
| EP | 1 270 025 | 1/2003 |
| EP | 1 277 450 | 1/2003 |
| WO | WO86/00526 | 1/1986 |
| WO | WO 91/08718 | 6/1991 |
| WO | WO95/24473 | 9/1995 |
| WO | WO95/31944 | 11/1995 |
| WO | WO98/52619 | 11/1998 |
| WO | WO99/37337 | 7/1999 |
| WO | WO 00/64504 | 11/2000 |
| WO | WO01/41825 A1 | 6/2001 |

OTHER PUBLICATIONS

Benjamin et al., "Conditional Switching of Vascular Endothelial Growth Factor (VEGF) Expression in Tumors: Induction of Endothelial Cell Shedding and Regression of Hemangioblastoma-like Vessels by VEGF Withdrawal", Proc. Natl. Acad. Sci. USA, vol. 94. pp. 8761-8766, Aug. 1997, Medical Sciences.

Bengtsson et al., "Endothelialization of Mechanical Heart Valves In Vitro with Cultured Adult Human, Cells", The Journal of Heart Valve Disease, vol. 2, No. 3, pp. 352-356, May 1993.

Van Belle et al., "Passivation of Metallic Stents After Arterial Gene Transfer of phVEGF$_{165}$Inhibits Thrombus Formation and Intimal Thickening", JACC vol. 29, No. 6, May 1997:1371-1379.

Van Belle et al., "Stent Endothelialization: Time Course, Impact of Local Catheter Delivery, Feasibility of Recombinant Protein Administration, and Response to Cytokine Expedition", Circulation, vol. 95. No. 2 Jan. 21, 1997, pp. 438-448.

Senger et al., "Stimulation of Endothelial Cell Migration by Vascular Permeability Factor/Vascular Endothelial Growth Factor through Cooperative Mechanisms Involving the $\alpha_V\beta_3$ Integrin, Osteopontin, and Thrombin", American Journal of Pathology, vol. 149, No. 1, Jul. 1996, pp. 293-305.

Asahara et al., "Synergistic Effect of Vascular Endothelial Growth Factor and Basic Fibroblast Growth Factor on Angiogenesis in Vivo", Supplemental II Circulation vol. 92, No. 9, Nov. 1, 1995, pp. 365-371.

Weatherford et al., "Vascular Endothelial Growth Factor and Heparin in a Biologic Glue Promotes Human Aortic Endothelial Cell Proliferation with Aortic Smooth Muscle Cell Inhibition", Surgery, vol. 120, No. 2, pp. 433-439 (Aug. 1996).

Spyridopoulos et al., "Vascular Endothelial Growth Factor Inhibits Endothelial Cell Apoptosis Induced by Tumor Necrosis Factor α: Balance Between Growth and Death Signals", J. Mol. Cell. Cardiol., vol. 29, 1321-1330 (1997).

Watanabe et al., "Vascular Permeability Factor/Vascular Endothelial Growth Factor Inhibits Anchorage-Disruption-Induced Apoptosis in Microvessel Endothelial Cells by Inducing Scaffold Formation", Experimental Cell Research 233, pp. 340-349 (1997).

Watanabe et al., "Vascular Permeability Factor/Vascular Endothelial Growth Factor (VPF/VEGF) Delays and Induces Escape from Senescence in Human Dermal Microvascular Endothelial Cells", Oncogene (1997) 14, 2025-2032.

* cited by examiner

VALVED PROSTHESIS WITH POROUS SUBSTRATE

ACKNOWLEDGEMENT OF GOVERNMENT SUPPORT

This invention was made with United States Government support under Cooperative Agreement Number 70NANB9H3000 awarded by the National Institute of Standards and Technology (NIST). The United States Government has certain rights in the invention.

FIELD OF THE INVENTION

The invention relates to valved prostheses, especially mechanical heart valve prostheses that are used to replace damaged or diseased native heart valves. In particular, the invention relates to valved prostheses with occluders that have pores to promote cell association with the prosthesis. In addition, the invention relates to medical devices formed from a porous material with hydrogel, structural protein and/or bioactive agents within the pores to present a smoother surface suitable for cell colonization.

BACKGROUND OF THE INVENTION

Physicians use a variety of prostheses to correct problems associated with the cardiovascular system, especially the heart. The ability to replace or repair diseased heart valves with prosthetic devices has provided surgeons with a method of treating heart valve deficiencies due to disease and congenital defects. One procedure involves removal of the native valve and surgical replacement with a prosthetic heart valve.

Prosthetic heart valves have leaflets or occluders that perform the function of opening and closing to regulate the blood flow through the heart valve. Typically, heart valve leaflets must either pivot or flex with each cycle of the heart to open and close the valve. Heart valves function as check valves, which open for flow in one direction and close in response to pressure differentials to limit reverse flow. Prostheses can be constructed from natural materials, synthetic materials or a combination thereof. Prostheses with rigid occluders generally include, for example, biocompatible metals, ceramics, carbonaceous solids, such as pyrolytic carbon, polymers and combinations thereof.

While prostheses with tissue leaflets are considered non-thrombogenic, mechanical heart valves with rigid occluders have the advantage of proven durability through decades of use. However, prostheses with rigid occluders are associated with potential blood clotting on or around the prosthetic valve and thromboembolism. Blood clotting can lead to acute or subacute dysfunction of the valve. For this reason, patients with mechanical heart valves remain on anticoagulants for as long as the valve remains implanted. Anticoagulants have associated risks and cannot be taken safely by certain individuals. Thus, there is an interest in providing mechanical heart valve prostheses with modified surface properties that can reduce thrombosis. Similar surface modification may be useful for other medical devices that contact body fluids.

SUMMARY OF THE INVENTION

In a first aspect, the invention pertains to an implantable prosthesis comprising a rigid material with pores. A filler comprising hydrogel, a structural protein and/or a biologically active molecule can be located within the pores. In embodiments of particular interest, the prosthesis is a mechanical heart valve including an orifice ring and a rigid occluder attached to the orifice ring.

In another aspect, the invention pertains to a mechanical heart valve prosthesis comprising an orifice ring and a rigid occluder attached to the orifice ring. The rigid occluder comprises a biocompatible material with pores. The biocompatible material comprises a polymer material, a carbonaceous solid or a ceramic. The pores extend through the occluder. The pores may or may not form an interconnecting network.

In a further aspect, the invention pertains to a method of forming an implantable prosthesis. The method can include forming pores in a rigid material in which the pore forming process selected from the group consisting of etching, mechanical striking of the surface, micromachining, dissolving of a soluble composition, heating a thermally decomposible material and using a foaming agent.

DETAILED DESCRIPTION OF THE INVENTION

Figure 1:
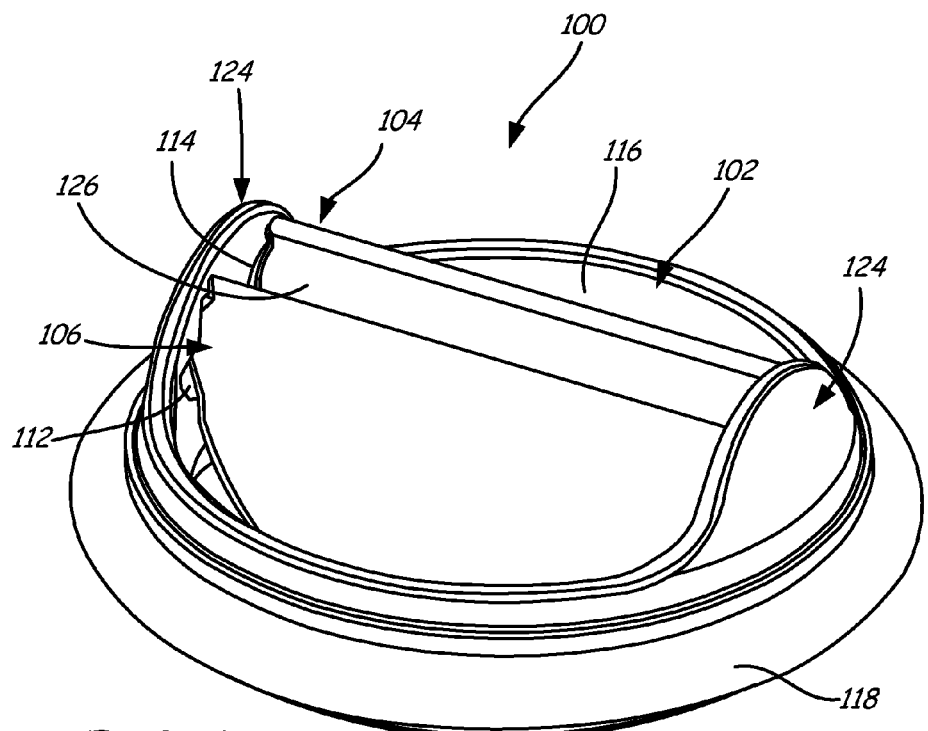
FIG. 1 is a perspective view of a bileaflet mechanical heart valve prosthesis.

An improved mechanical heart valve prosthesis with a rigid occluder/leaflet includes a porous, rigid material to facilitate ingrowth of viable cells. In some embodiments, the occluder includes the rigid porous material. In addition, the pores can include a hydrogel to present a smoother surface for fluid flow while maintaining the capability of supporting cell ingrowth. Some structural proteins have properties similar to synthetic hydrogels and can be similarly used. The occluder can be produced from rigid materials, such as metal, ceramics, carbonaceous solids and polymers, although polymers are of particular interest. With polymer occluders, impact loadings at closure of the occluder can be reduced. The polymers should be durable with adequate mechanical strength. In some embodiments, the pores can include bioactive agents to encourage cell population of the substrate surface. While the discussion herein focuses on the processing of rigid occluders and components of valved prostheses, several features of the invention, such as inclusion of a hydrogel or structural protein composition within pores, can be useful for other medical devices that contact body fluids. Bioactive agents can also be incorporated within the porous structure with or without the inclusion of a hydrogel/structural protein.

In general, heart valve prostheses can include flexible leaflets or a rigid occluder to block flow back through the valve upon valve closure. Heart valve prostheses with rigid occluders are of particular interest herein. The valve operates as a one way check valve with the occluder pivoting to open the valve to allow forward flow. In response to pressure changes, the occluders close across the valve lumen to restrict backflow. The rigid occluders attach to an orifice ring that forms the valve lumen. The one or more occluders attach to the orifice ring at a pivot or hinge. The valve can include a pivot guard or other comparable structures.

Mechanical heart valve prostheses may be associated with thrombosis. For typical mechanical valves with occluders formed from rigid, durable materials, the presence of the rigid occluder(s) disturbs the blood flow and may lead to regions of re-circulation or slow blood flow. The surface next to the regions of flow separation may be susceptible to thrombus formation and adhesion of the thrombus to the valve surface.

In the preferred embodiments, the rigid occluder(s), the orifice ring and/or other rigid components of the mechanical valve or other medical devices have a porous structure to provide for cellular attachment and proliferation. With attachment sites at the surface, cellular proliferation can more easily spread across the porous surface, forming a tissue interface. The presence of the cells/tissue reduces the tendency of thrombus to adhere to the valve surface, which results in improved blood compatibility of the surface. Therefore, the valve, with viable cells associated with the occluder and/or the orifice ring, is expected to have reduced thrombosis. In alternative embodiments, portions of the prosthesis can include porosity for facilitating cellular attachment. In particular, the valve ring and/or the pivot guards can have a porous structure.

The pores provide suitable attachment points for colonization by viable cells. While the porous structure may or may not extend beyond the surface into the rigid material, in preferred embodiments, the pores extend significantly into the occluder material or through the occluder material to provide improved anchoring for the cells. Preferred embodiments include a hydrogel, structural protein and/or bioactive agent filler within the pores. Hydrogels and/or structural proteins within the pores can present a smoother surface to the flow and prevent flow through pores extending through the rigid material. In alternative embodiments without filler, the porous structure, if it extends through the rigid porous material, should not provide for significant blood flow through the material since the valves are intended to block blood flow when the one or more occluders are closed within the valve lumen. Nevertheless, if the pores are sufficiently small, they may extend through the porous material, even without filler, without allowing significant blood flow through the material. Also, cellular growth will further function to block any blood flow through porous material. If filler is located within the pores, pore size can be larger than embodiments without a filler material, even if the pores extend through the porous material. Having pores that extend through the porous material with a filler may facilitate entry of cells into the structure for colonization.

To provide extensive coverage of cells over the surface of the rigid material, the pores generally cover the surface at relatively high density. However, the presence of the pores as colonization points for cells can lead to additional cell proliferation across extended regions of the surface between pores. Thus, average pore distances can be selected based on factors such as the rate of cell colonization of the porous surface, the degree of cell colonization support provided by the pores and the effect on blood flow of the pores. In addition, pores have an appropriate average diameter to encourage cellular attachment. Generally, the pores have an average diameter greater than the average cell diameter such that cells can enter or partly enter the pores to anchor.

In general, the components of a mechanical heart valve with a rigid occluder can be constructed from any rigid material that is biocompatible. For example, rigid occluders and orifice rings can be formed from metals, ceramics, polymers and carbonaceous solids. However, some materials may have better levels of blood compatibility and resistance to thrombosis. Carbonaceous solids, such as pyrolytic carbon, have proven to be desirable materials due to their durability and blood compatibility features. Other suitable materials for rigid occluders include, for example, metals including various alloys. Rigid polymers can be a preferred material for the production of rigid occluders. Suitable rigid polymers have a desired level of durability. Since polymers are generally less stiff than metals and ceramics, polymer materials inherently have reduced impact loading and correspondingly reduced pressure spikes when the valve closes.

The presence of pores in the rigid material can promote cellular attachment. However, the presence of the pores can also affect flow along the surface of the occluder, the orifice ring and/or other valve components, or other device components. Specifically, the pores can induce some turbulence into the flow along the surface of the occluder or component. To gain the advantages of the pores for cellular attachment without presenting a rough surface to the blood flow, the pores can be filled, completely or in part, with a hydrophilic polymer that swells with water, i.e., a hydrogel. The hydrophilic hydrogel polymer provides a smooth surface along the occluder for blood flow while simultaneously providing a matrix for cellular attachment. Preferred hydrogels have a structure that would be conducive to infiltration by cells. In particular, hydrogels generally are crosslinked and have molecular weights and chemical functionality that provide significant hydration through the polymer structure. Hydrogels are generally stable pore filling materials that do not migrate. Bioresorbable hydrogels generally resorb in a gradual, predictable manner that can be correlated with cellular ingrowth for replacement of the hydrogel with cellular material.

Alternatively, or in addition, the pores can be filled, completely or in part, with extracellular matrix proteins or other structural proteins. Extracellular matrix proteins are proteins secreted by cells to form the extracellular matrix of tissue. Collagen generally is a primary component of the extracellular matrix. Depending on the tissue, the extracellular matrix can include other proteins and carbohydrates, such as elastin and proteoglycans. Suitable extracellular matrix compositions for placement into the pores include purified forms of the proteins, especially collagen, as well as natural extracellular matrix materials that have been purified and/or modified, for example, by chemical crosslinking. Other comparable structural proteins can also be used. Suitable structural proteins are insoluble in water, but are characterized by a hydrophilic character of the outer portions of the protein such that the matrix swells with water.

The presence of a hydrogel or structural proteins in the pores can assist with cell colonization by providing an effective anchoring material for cell attachment. While effectively filling the pores with hydrogels, structural proteins or combinations thereof provides a smooth surface for the flow, partly filling the pores with lesser amounts of material may be adequate to reduce any disruption of the flow due to the pores. In addition, the presence of hydrogel and/or structural proteins may fill pores passing through the occluder to prevent leakage of blood. The hydrogel and/or structural proteins can include nutrients to stimulate cell colonization. Suitable nutrients include, for example, glucose, amino acids and vitamins.

Furthermore, bioactive agents can be included in the pores, with or without hydrogels and/or structural proteins for cellular attachment. Suitable bioactive agents include, for example, anticoagulants, growth factors and cell binding compounds that bind to progenitor cells. Anticoagulants can counter thrombogenic aspects of the valve. Growth factors and cell binding compounds can stimulate cell colonization of the associated surface, whether the surface is part of a rigid occluder or other medical device or component thereof.

Desirable cell types for attachment to the valve include fibroblast cells, i.e., fibroblasts, and endothelial cells, such as vascular endothelial cells. Fibroblast cells secret and maintain the extracellular matrix in tissue. Thus, the presence of fibroblast cells on the valve surface can provide and/or maintain an extracellular tissue-like matrix material within the pores and/or along the remaining portions of the valve surface if the cells spread beyond the pores. Vascular endothelial cells form the surface of vascular tissue in a thin layer approximately one cell thick. The fibroblast cells may form or maintain a suitable matrix for colonization by endothelial cells such that a stable, self-maintaining material can be formed with both types of cells. A surface layer of endothelial cells provides a particularly good antithrombogenic surface.

In general, the valve or other medical device having rigid material prepared for cell adhesion is implanted into the patient. Once implanted, circulating cells and adjoining cells near the implantation site from the patient can colonize the porous, rigid material. Using an in vivo colonization approach, the patient's own cells grow on the prosthesis. The nature of the colonization process should select for appropriate cell types for colonization of the porous surface. Thus, rejection by the patient's immune system does not result from the presence of foreign cells. Once the rigid material is colonized by the cells, the rigid material can present improved hemodynamics while having improved biocompatibility. Thus, the surface properties due to the presence of the cells can improve with respect to blood flow following cell colonization.

Alternatively, the occluder and/or other portions of the prosthesis can be colonized with cells in vitro. Specifically, the heart valve or components thereof can be placed in a cell culture system such that the heart valve components can be colonized by cells using tissue culture techniques. In these embodiments, the cells for the cell culture system can be obtained from the patient that is the ultimate recipient of the prosthesis. If the patient's cells are used in the cell culture system, the risk of later rejection is reduced significantly or eliminated. The in vitro cell colonization procedure can be performed shortly before implantation of the prosthesis to avoid long term maintenance of the tissue with the cells and to simplify logistics with respect to the specific patient/cell donor. Alternatively, cells from another donor can be used for in vitro colonization, generally so that the cells are selected using accepted blood factors for establishing an acceptable level of compatibility.

Processes for the formation of the porous material are selected based on the composition of the material, the desired pore characteristics and the approach for the formation of the material. For the formation of porous rigid occluders in some materials, a salt leaching technique can be used. For example, a soluble particulate material can be introduced into the material while it is being formed. If the porous material is formed under conditions in which the particulates are not dissolved, the rigid material can be contacted with an appropriate solvent that does not dissolve the rigid structure but will dissolve the particulates after the material is formed. Dissolving and removing the particulates results in the formation of pores in the rigid material. Similarly, particulates can be used that are heat sensitive such that heating causes the removal of the particulates. In addition, pores can be introduced through the formation of gas bubbles in the material when it is being formed. For example, foaming agents can be used to introduce gas bubbles in polymer melts that solidify into porous polymer materials.

Alternatively, for rigid materials, pore formation can take place using a mask or photolithography to protect the surface while pores are formed by sputtering or the like. Similar approaches are used in semiconductor processing to form structures on surfaces. Similarly, micromachining can be performed to produce an ordered array of pores of specified characteristics. Micromachining involves precision etching with focused beams, such as laser beams or electron beams, to pattern the surface of the material.

Medical Devices

Relevant biocompatible medical devices using the porous materials described herein include all medical articles that contact body fluids and/or tissues. Medical devices of particular interest, or components thereof, which are formed with the porous material, are generally rigid or stiff. The medical devices can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane, such as within a patient's mouth.

Implanted medical devices include, without limitation, prostheses such as heart valve prostheses, pacemakers, defibrillators, artificial organs such as artificial hearts, ventricular assist devices, anatomical reconstruction prostheses such as dental implants, surgical patches or plates, coronary stents, vascular, cardiovascular and structural stents, vascular and cardiovascular shunts, pledgets, annuloplasty rings, stents, staples, connectors, electrical leads such as pacing leads, valved grafts, orthopedic or spinal implants, orthopedic pins, intrauterine devices (IUDs), urinary stents, permanently indwelling percutaneous devices, maxial facial reconstruction plating, clips, bone, orthopedic prostheses, and combinations thereof.

Percutaneous medical devices include, without limitation, cannulas, introducers, and drainage tubes such as chest tubes. Cutaneous medical devices include, without limitation, dental hardware, such as bridge supports and bracing components.

While the porous rigid materials can be used in any of the medical articles described above, valved prostheses are of particular interest. More specifically, components of mechanical valves can advantageously be formed from the porous rigid materials described herein. In particular, the mechanical valves can be used in artificial hearts, heart valve prostheses, valved prostheses or left ventricular assist devices. The rigid occluders pivot to open and close, which controls flow through the valve. Heart valve prostheses with rigid occluders are suitable for the replacement of damaged or diseased native heart valves.

Mammalian veins include valves that assist with blood circulation by limiting the amount of back flow in the veins. Veins collect blood from capillaries and are responsible for returning blood to the heart. Generally, vascular valves are replaced as part of a vascular graft with sections of conduit.

A bileaflet mechanical heart valve prosthesis 100 is shown in FIG. 1. Heart valve prosthesis 100 includes an orifice ring 102, which retains two occluders 104, 106. Occluders 104, 106 rotate at pivots 112, 114 and two additional opposed pivots symmetrically positioned on the inner luminal surface 116 of orifice ring 102 (not shown). Inner luminal surface 116 of orifice ring 102 forms a flow path through the valve that can be opened or closed through the pivoting of occluders 104, 106. A sewing cuff 118 is placed around orifice ring 102 to facilitate attachment with the patient's tissue during implantation of the valve. In the embodiment shown in FIG. 1, orifice ring 102 has a pivot guard structure 124, which projects upstream of the plane of orifice ring 102.

Blood flows through valve 100 in an effectively unidirectional way. Occluders 104, 106, shown in the open position in FIG. 1, pivot in response to forces imparted by the blood during the cardiac cycle. Occluders 104, 106 cyclically close to effectively block back flow through the valve lumen. In the closed position, downstream surfaces of occluders 104, 106 block back flow through the valve. Downstream surface 126 of occluder 104 is shown in FIG. 1. Occluders 104, 106 subsequently assume an open position to allow forward flow through the valve lumen.

All or a portion of occluders 104, 106 can be formed from the porous materials described herein. Additionally, or alternatively, all or a portion of ring 102 can be formed from the porous materials. If formed from the porous materials, especially with hydrogel, structural protein filler and/or bioactive agent, the blood contacting surfaces of valve 100 can be colonized more easily by viable cells, which are maintained by nutrients in the blood flow. Blood contacting surfaces include the surfaces of occluders 104, 106 and inner luminal surface 116 of orifice ring 102.

Figure 2:
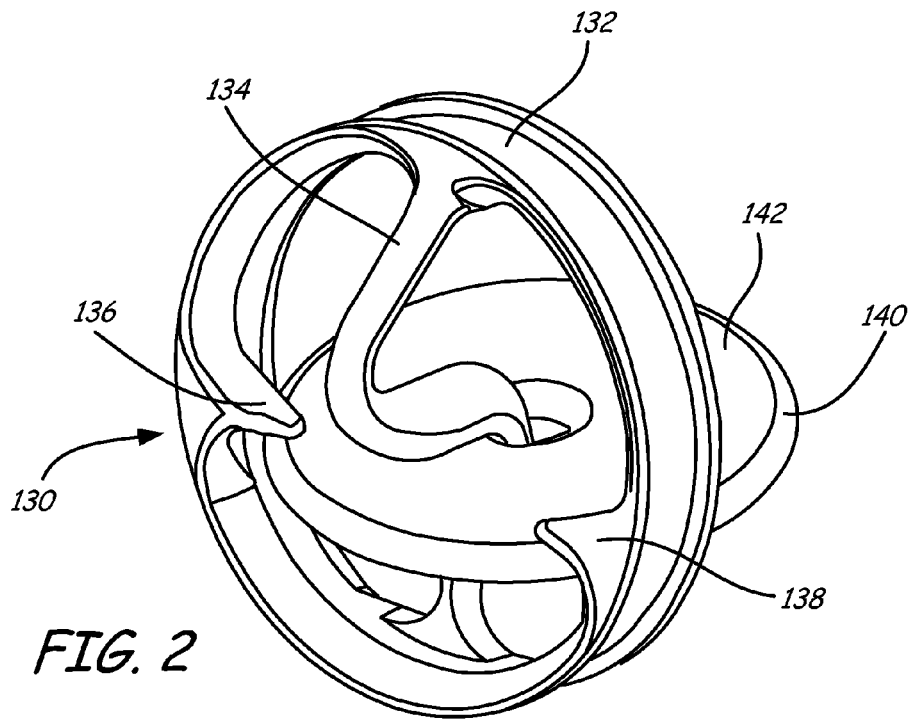
FIG. 2 is a perspective view of a single occluder heart valve prosthesis.

The porous materials can be used to form different embodiments of mechanical heart valves. For instance, a single-occluder mechanical heart valve prosthesis 130 is shown in FIG. 2. Heart valve prosthesis 130 includes an orifice ring 132 with a pivot arm 134 and two stops 136, 138. Occluder 140 can swing on pivot arm 134 to move between a closed position, and an open position, as shown in FIG. 2. At a fully open position, the swinging motion of occluder 140 is halted by stops 136, 138. Occluder 140 can be formed from porous materials to provide for cell ingrowth. Similarly, other portions of valve 130 can be formed from the porous materials, such as orifice ring 132. Blood flow through valve 130 is effectively unidirectional such that the valve closes with upstream surface 142 of occluder 140 blocking back flow through the valve.

Figure 3:
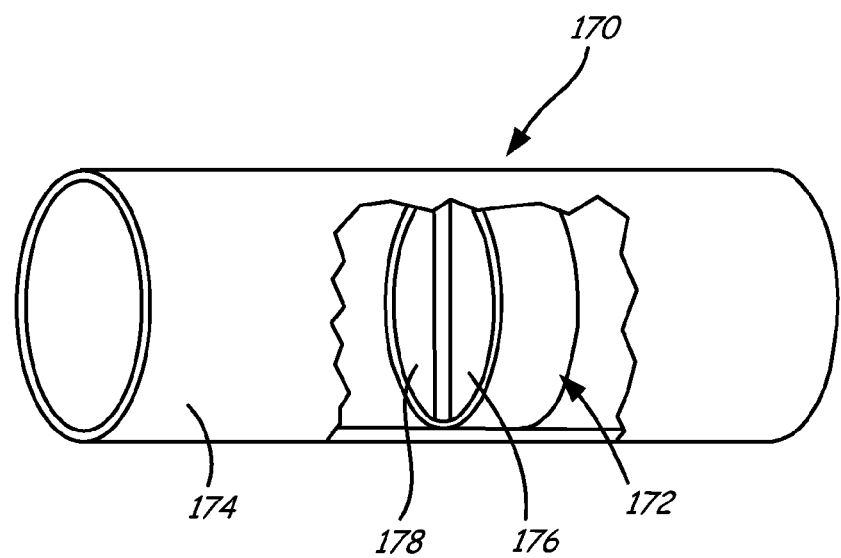
FIG. 3 is a perspective view of a valved prosthesis with a mechanical valve.

A valve with one or more porous rigid occluders can be incorporated into a graft for replacement of a venous valve or for the replacement of an aortic or pulmonary heart valve. A valved prosthesis 170 is shown in a fragmentary view in FIG. 3. Prosthesis 170 includes a valve structure 172 in a conduit 174. Valve structure 172 includes rigid occluders 176, 178, although the number of occluders can vary. Conduit 174 can be made from natural materials, such as fixed bovine pericardium, or synthetic materials, such as polymers, for example, polyesters.

Figure 4:
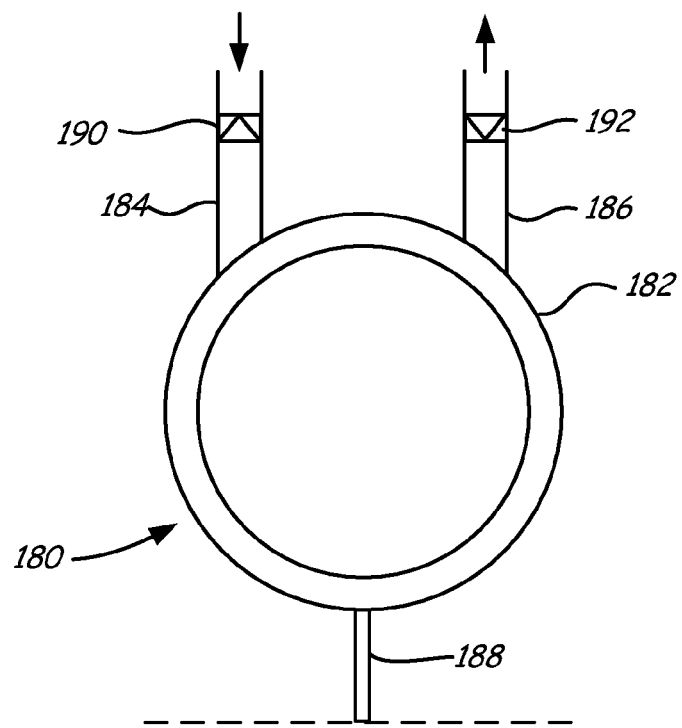
FIG. 4 is a schematic side view of a left ventricular assist device with two mechanical valves.

In addition, a valve with one or more porous rigid occluders can be incorporated into a left ventricular assist device 180, as shown in FIG. 4. Left ventricular assist devices are implanted devices generally used to maintain the ventricular pumping function of a patient with a damaged or diseased heart awaiting a heart transplant. Referring to FIG. 4, left ventricular assist device 180 includes a drive unit 182, an inflow tube 184, an outflow tube 186 and connection 188. Drive unit 182 includes a pump to provide pulsatile flow from inflow tube 184 to outflow tube 186. Connection 188 provides for electrical or pneumatic control signals to be directed to the drive unit from a controller and power supply, generally external to the patient. Inflow tube 184 includes an inflow valve 190, and outflow tube 186 includes an outflow valve 192. Arrows depict the direction of blood flow through inflow tube 184 and outflow tube 186 as controlled by valves 190, 192. Either one or both of inflow valve 190 and outflow valve 192 can be a valve with one or more porous rigid occluders.

Biocompatible Materials

Relevant medical articles can include one or more biocompatible materials. Specifically, the medical devices may include, for example, tissue or tissue-derived material, natural or synthetic polymers, other synthetic materials, and combinations and composites thereof. At least one of the materials forming the medical device is a rigid material with pores. Specifically, for mechanical heart valve embodiments, a rigid occluder and/or other rigid components generally includes a material with pores. Features of biocompatible materials, which may or may not be porous, are discussed generally in this section, while the nature of the pores is discussed in the following section.

Rigid materials are materials that do not deform with a visible shape change upon contact with a vascular system experiencing physiologic blood pressure, generally below about 200 mmHg. For a valve with a rigid occluder, functioning of the valve is dependent on the lack of deformation of the leaflet. This description of rigid materials can be used for medical devices and components thereof even if they do not themselves contact the vascular system. Of course, rigidity is a function of composition as well as processing, dimensions and other features of the material.

In general, biocompatible materials can be formed from natural materials, synthetic materials or combinations thereof. While porous rigid material is of particular interest, other materials in medical devices can be formed from nonporous rigid material and/or flexible material. For example, flexible materials, such as polyesters, can be used to form a variety of medical device components, such as sewing cuffs and the like.

Relevant rigid materials generally include, for example, polymers, metals, carbonaceous solids and ceramics. Ceramics are intended to have a broad meaning, including, for example, metal compounds, such as metal oxides and metal carbides, and/or silicon compounds, such as silicon oxides and silicon carbides. Specifically, appropriate ceramics include, for example, hydroxyapatite, metal carbides, silicon carbides, zirconia and alumina. Relevant carbonaceous solids include, for example, graphite, turbostratic carbon and pyrolytic carbon. Metals are intended to include elemental metals in their unreacted forms, metal alloys and elemental metals and alloys with small quantities of property modifiers, such as carbon, as long as the resulting material has metallic properties. Suitable inert metals include, for example, titanium, cobalt, stainless steel, nickel, iron alloys, cobalt alloys, such as Elgiloy®, a cobalt-chromium-nickel-molybdenum-iron alloy, and MP35N, a nickel-cobalt-chromium-molybdenum alloy, and titanium alloys, such as Nitinol®, a nickel-titanium alloy.

While thickness and geometry can affect flexibility/rigidity of a material, composition can play a significant role, especially with polymer materials. Preferred rigid polymers for forming polymer members include, for example, polysulfones, polyacetals (e.g., Delrin®), polyethersulfones, polyarylsulfones, polyetheretherketones, polyamides (nylon), polyurethanes, polytetrafluoroethylene, other fluoronated and perfluoronated vinylpolymers, polycarbonate, polyetherimides, tyrosine-derived polyarylate polymers, polylactic acid and polyglycolic acid-based composites (PLLA-PGA), polyhydroxybutrate-based polymers and copolymers and mixtures thereof. These polymers are suitable for the formation of rigid occluders. The polymer materials can be molded, extruded, cast or similarly processed into appropriate forms.

Porosity

At least a portion of the medical device includes a porous material to provide for ingrowth of viable cells. The pores may or may not establish a network of interconnecting porosity. The pores can be arranged in an orderly array or can be randomly distributed with respect to the surface. The pores extend over the regions of the porous material at which cell growth is desirable. The pores should be large enough to provide for cellular attachment. In addition, the pores preferably do not excessively disrupt flow along the surface. However, the presence of hydrogel and/or structural protein filler within the pores reduces or eliminates any disruption of the blood flow due to the pores.

In general, the pores can be limited to the surface to provide cell colonization at the material surface. However, in preferred embodiments, the pores extend beyond the surface into the bulk of the porous material or even through the porous material to provide for more extensive cellular ingrowth or for processing convenience. The presence of a network of pores through the material can provide for the development of an extracellular matrix through the network following colonization with cells. The extracellular matrix can replace or supplement a hydrogel or exogenous, i.e., non-native, structural proteins that are deposited into the pores prior to implantation.

However, any porous network extending through the material should not provide significant blood flow through the porous material. In preferred embodiments, the addition of hydrogels and/or structural protein fillers to the pores inhibits or eliminates any flow through pores extending through the rigid occluder material. In addition, if the pores have a small diameter, any flow through the pores would be restricted. Cellular ingrowth would inherently restrict subsequent flow through the pores through the presence of cells in the pores and/or through the formation of natural extracellular matrix material produced by the cells. Pores extending into or through the porous material may be desirable to provide more extensive cellular ingrowth to support additional anchoring of cells.

The pores can extend over the entire surface of an element or component or over a selected portion of the surface. In particular, if cellular colonization is desired over a selected portion of a material, the pores can be placed over the selected portion of the surface. The density of pores along the surface is balanced between providing a better surface for cellular colonization and altering flow along the surface prior to cell colonization. Specifically, a higher density of pores provides more locations for cellular colonization. In preferred embodiments, the placement of hydrophilic materials within the pores can reduce or eliminate any disruption of the flow due to the presence of a higher density of pores.

Generally, the pores have a depth and diameter sufficiently large for a cell or a portion thereof to fit within the pores. Generally, the average pore diameter ranges from about 10 microns to about 1 millimeter, and in other embodiments from about 25 microns to about 500 microns. Similarly, the pores preferably have an average depth of at least about 5 microns and in many embodiments, at least about 25 microns. For materials with a porous network through the material, the pore depth may not be particularly relevant. The shape of the pores generally depends on the method for forming the pores.

For preferred embodiments with pores extending through the porous material, the pores can go straight through the material. Alternatively, the pores can form a network that winds through the material from one surface to the other. The network may or may not have branches. An occluder, for example, generally has a thickness from about 500 microns to about 5 millimeters. The method for forming the pores generally determines the nature of the pores extending through the porous material.

Hydrogels

The pores of the porous materials can be filled or partly filled with hydrophilic polymer to present a smoother surface to the fluid flow over the material. Thus, the hydrophilic polymer modified porous material is less disruptive to flow past the material. Preferred hydrophilic polymers, i.e. hydrogels, swell with water on contact. The hydrophilic character of the pore filling polymer is in contrast with the characteristic of most rigid materials. The hydrogel may provide a matrix for cell ingrowth into the hydrogel material or, at least, for facilitating cellular attachment within the pores of the material.

Hydrogels are polymers, in their hydrated state, that are swollen with water, but do not dissolve in the water. The hydrogel polymers are usually crosslinked. The crosslinked polymers form a three-dimensional polymer network in which the hydrophilic nature of the monomers promotes the swelling with water while the crosslinking thwarts the tendency of the swollen polymer to dissolve. Hydrogels can be formed from natural or synthetic polymers. Hydrogels may or may not irreversibly modify when dried out. Hydrogels have been used in various medical applications, such as contact lenses and wound dressings.

Suitable polymers for the formation of hydrogels include, for example, poly(ethylene glycol), poly(hydroxyethyl methacrylate), partially or fully hydrolyzed poly(vinyl alcohol), poly(vinylpyrrolidone), poly(ethyloxazoline), poly(ethylene oxide)-co-poly(propylene oxide) block copolymers, poloxamines, polyacrylamide, hydroxypropylmethacrylate (HPMA), carboxymethyl cellulose, hydroxyethyl cellulose, methylhydroxypropyl cellulose, polysucrose, hyaluronic acid, chondroitin sulphate, dextran, sodium alginate, derivatives of alginate, chitosan, derivatives of chitosan and mixtures and copolymers thereof. Alginate and chitosan are natural polysaccharides that can be crosslinked with polyfunctional anions, such as dicarboxylic acids, sulphate ions and carbonate ions. Some of these polymers are bioresorbable, i.e., the polymers gradually degrade following implantation into the patient. For example, hyaluronic acid and derivatives thereof are bioresorbable. Modified forms of hyaluronic acid can be adjusted to select the degree of crosslinking and rate of resorption. Resorbable hydrogels can be gradually replaced with cellular material as the hydrogel is colonized by cells. The use of hydrogels for supporting cell growth is described further in U.S. Pat. No. 6,224,893 to Langer et al., entitled "Semi-Interpenetrating Or Interpenetrating Polymer Networks For Drug Delivery And Tissue Engineering," incorporated herein by reference.

The hydrogels may partly or completely fill the pores. The presence of the hydrogels can reduce any disruption of flow over the surface due to the presence of the porosity. Approximately complete filling of the pores presents a relatively smooth surface to the flow, although partially filled pores may present a sufficiently smooth surface to reduce or eliminate effects of the pores on the fluid flow past the surface. In addition, the hydrogels can be placed within the pores of the rigid material to form a matrix for cell colonization. Specifically, the hydrogels can form an adhesion material to which the cells can anchor.

To place the hydrogels within the pores, the porous material can be dipped and removed from a solution containing monomers and/or uncrosslinked polymer prior to polymerization and/or crosslinking. Then, the material can be polymerized/crosslinked by contacting the material with a chemical crosslinking agent, a free radical initiator to catalyze a free radical crosslinking or appropriate radiation, such as an electron beam or ultraviolet light. Alternatively, the hydrogel can be spread or sprayed over the porous surface to absorb into the pores. Hydrogel may also cover portions of the surface between the pores.

Structural Protein Fillers

Structural proteins can also be placed within the pores to smooth the surface for flow past the surface and to serve as an attachment material for cells. Thus, the structural proteins serve as functional alternatives to hydrogels. Suitable structural proteins include extracellular matrix proteins as well as other structural proteins. Structural proteins are characterized by hydrophilic proteins that provide an insoluble matrix for cell adhesion. Proteins can be crosslinked to provide structural stabilization and/or to render the proteins insoluble but hydrophilic. The structural proteins can be combined with hydrogels and/or bioactive agents for forming a pore filling or partially pore filling matrix.

Proteins are intended to broadly cover polypeptides and multi-subunit polypeptides and derivatives thereof, including polypeptides that are covalently or noncovalently associated with carbohydrates, fatty acids, nucleic acids and other compositions. Proteins include crosslinked polypeptides that are crosslinked either naturally or synthetically. Synthetic crosslinking of proteins can involve added chemical crosslinking agents. Structural proteins include proteins that are hydrophilic or have hydrophilic domains and are not soluble in water under physiological conditions without the application of vigorous mixing. Structural proteins form suitable matrices for cellular colonization. Cellular colonization may further stabilize the structural protein matrix. Mixtures of proteins can be used as structural proteins.

Suitable proteins include, for example, proteins found in the extracellular matrix. These proteins form a structural component of tissue and are inherently a suitable cell colonization structure. For many tissues, collagen is a major component of the extracellular matrix. Collagen has an unusual amino acid composition and forms fibrils with a helical structure. Collagen protein can form a stiff structure and can be combined with other proteins to modify the nature of the extracellular matrix. Gelatin is a modified form of collagen and can be considered a structural protein. Other extracellular matrix proteins include, for example, elastin, protein mimicking polypeptides and proteoglycans, which are also suitable structural proteins.

Some natural proteins include crosslinking between subunits. It may be desirable to chemically crosslink desirable proteins to form a structural protein matrix. For example, albumin is a prevalent water soluble protein that serves at least as a fatty acid transported in plasma. The crosslinking of albumin can be used to form a non-water soluble matrix of protein with hydrophilic domains. Due to the availability of serum albumin, it may be a convenient source of structural proteins. Similarly, it may be desirable to crosslink extracellular matrix proteins, such as collagen, to stabilize the protein against proteolysis and denaturation and/or to modify the properties of the matrix.

Protein crosslinking involves the use of multifunctional compounds that bind with amino acid side chains within the proteins. Glutaraldehyde is a commonly used protein crosslinking agent, but other crosslinking agents can be used, such as other difunctional aldehydes, epoxides, genipin and derivatives thereof.

As with hydrogels, the structural proteins may partially or completely fill the pores. In addition, the structural proteins can be combined with hydrogels and/or bioactive agents to fill pores. The mixture can combine desirable properties of both materials. The amount of each material can be selected to yield the desired properties of the combined material. Similarly, hydrogels and structural proteins can be applied sequentially within the pores to form a composite without necessarily mixing the materials. In other words, the inner portion of the pores can be filled with a first pore filling material while an outer portion of the pores can include another pore filling material. The combined materials may or may not completely fill the pores.

While the structural proteins are selected to be insoluble under physiological conditions, the proteins may be soluble in water at nonphysiological pH or under vigorous mixing in dilute solutions. Thus, the porous material can be contacted with a solution of the structural proteins followed by a precipitation of the proteins by changing the conditions of the solution, such as the pH, or by removing the solvent and drying the material through evaporation. Alternatively, if the proteins are initially soluble, the porous material can be contacted first with a solution of the protein to associate the protein with the material and then with a crosslinking agent to reduce or eliminate the solubility of the protein to form the structural protein material, which is insoluble in water. For the placement of a combination of both structural proteins and hydrogels in the pores, the above application methods for the separate placement of structural proteins and hydrogels can be combined. Some adjustment to the methods can be performed based on the relative amounts of each material.

Bioactive Agents

The pores of the medical device can be associated with a bioactive agent, i.e., biologically active compounds to impart biologically relevant characteristics to the surface. In particular, the pores can be treated to stimulate the association of desirable cells with the surface, to promote the proliferation of associated cells and/or to reduce coagulation in the vicinity of the medical device following contact with body fluids and/or tissue. The bioactive agents can be placed within the pores alone or in combination with hydrogels and/or structural proteins. The presence of a hydrogel and/or structural proteins in the pores in preferred embodiments can improve the retention of bioactive agents and can increase the amount of bioactive agents that can be effectively associated with the porous material.

For example, pores of a prosthesis can be associated with one or more cytokines, growth factors, such as vascular endothelial growth factor (VEGF) and/or fibroblast growth factor, and/or attraction compounds that recruit cells, including progenitor cells, to the material. VEGF refers to a family of polypeptides that have been found to preferentially stimulate growth of vascular endothelial cells over other cells, such as smooth muscle cells. Several iso-forms of VEGF have been identified. VEGF has also been referred to as vascular permeability factor. Human recombinant $VEGF_{165}$ is available commercially from R&D Systems, Minneapolis, Minn.

The use of VEGF in the manufacture of tissue-containing prostheses has been described further in copending and commonly assigned U.S. patent applications Ser. No. 09/014,087 to Carlyle et al., entitled "Prostheses With Associated Growth Factors," and Ser. No. 09/186,810 to Carlyle et al., entitled "Prostheses With Associated Growth Factors," both of which are incorporated herein by reference. Also, the association of VEGF and/or structural proteins with ceramics and carbonaceous solids in medical devices is described further in copending and commonly assigned U.S. Pat. No. 09/459,451 to Carlyle et al., entitled "Medical Articles Prepared For Cell Adhesion," incorporated herein by reference.

For the attraction of progenitor cells, desirable progenitor cells include both stem cells and progenitor cells that have the potential to differentiate into the cells of interest, including fibroblasts or endothelial cells. Some progenitor cells circulate in a patient's blood stream, while others may be mobilized from other sites in the body or infused into the circulation. These progenitor cells are thus available to colonize suitable blood contacting materials. Suitable progenitor cells can be selected from the blood stream and associated with the porous material. To initiate the colonization by the progenitor cells, an attraction compound can be associated with the material. An attraction compound is selected to bind to the progenitor cells. Suitable attraction compounds include, for example, antibodies and ligands that bond to antigens or receptors on the progenitor cells. Circulating progenitor cells may be removed from circulation by the attraction compound and become associated with the substrate. The use of attraction compounds, such as antibodies and ligands, to associate progenitor cells with a substrate is described further in copending and commonly assigned U.S. patent application Ser. No. 09/203,052 to Carlyle et al., entitled "Substrates For Forming Synthetic Tissue," incorporated herein by reference.

In addition, anticoagulants can be useful to reduce the risk of thrombosis due to the implantation of the medical device. This treatment can be especially useful in the period following implantation prior to cellular colonization of the medical device. Suitable anticoagulants include, for example, heparin, Coumadin® (sodium salt of warfarin) and derivatives and combinations thereof.

If the bioactive agent is included within a hydrogel and/or structural protein matrix, the hydrogel and/or structural protein can help to maintain the bioactive agent within the pores. The bioactive agents can mixed with the hydrogels and/or structural proteins prior to applying the hydrogels/structural proteins to the porous surface. Alternatively, the bioactive agents can be contacted with the hydrogels/structural proteins after they are placed within the pores. If additional binding within the pores is desired, the bioactive agents can be chemically bonded to the hydrogel and/or structural proteins with a crosslinking agent or other chemical binding agent. If the bioactive agents are proteins to be bonded to structural proteins, standard protein crosslinking agents, as described above, may be useful. For hydrogels, appropriate crosslinking agents can be selected based on the chemical composition of the hydrogel. At least one functional group of the crosslinking agent would be selected to bind to the protein, such as an aldehyde group, while another functional group of the crosslinking agent would be selected to bind to the hydrogel.

For embodiments with no hydrogel or structural proteins, the association of a bioactive agent or agents with pores of the rigid material each may involve direct attachment, application with an adhesive or binder, or chemical binding involving a binding agent in addition to the attraction compound/response modifier. For some materials, the bioactive agent may directly associate with the surface. This direct attachment may involve adsorption onto the pores with electrostatic attractions, such as van der Waals forces and hydrogen bonding. Direct attachment may also involve covalent or noncovalent bonding between functional groups present in the bioactive agent and the porous material without the addition of a crosslinking agent. Direct attachment can be suitable for some polymer materials, ceramic materials and carbonaceous solids. Direct attachment entails combining the substrate with a solution of the bioactive agent(s) without the use of an additional chemical binder or crosslinking agent.

In embodiments involving the use of an adhesive, the bioactive agent(s) associates with the substrate due to incorporation into the structure of the adhesive. Suitable adhesives include, for example, biologic glues such as fibrin glue, and the like. Fibrin glue can be formed from the polymerization of fibrinogen and thrombin. Suitable fibrin glues are available from, for example, Immuno AG, Austria, and can be obtained from various blood banks. Other available surgical adhesives are generally suitable. The use of an adhesive can be effective generally with any porous material.

In other embodiments, the association of a bioactive agent(s) with the substrate involves chemical binding initiated by a selected chemical reagent, a chemical binding agent. In contrast to the use of an adhesive, chemical binding involves specific molecular interactions with compositions in the crosslinked tissue, rather than a collective adhesion. Chemical binding can involve covalent bonding, a plurality of noncovalent chemical interactions, or a combination of both covalent and noncovalent interactions. Noncovalent chemical interactions include ionic bonding, hydrogen bonding, van der Waals interactions and molecular rearrangements, which characterize specific binding interactions, such as antibody-antigen interactions, protein-receptor binding and enzyme-substrate associations. Covalent bonding involves the use of a crosslinking agent. The crosslinking agent generally is selected to have at least one functional group that bonds to the bioactive agent, such as an aldehyde group if the bioactive agent is a protein, and at least one functional group that bonds to the porous material.

Formation of Materials with Porosity

The improved rigid materials described herein have a porosity, which may or may not extend through the material. While some approaches for forming the rigid structures, such as casting, molding and machining, may introduce porosity if appropriately modified, such as placing bumps in a mold, porosity generally is introduced more conveniently following formation of the material. Suitable approaches for introducing porosity generally depend on the nature of the material. Any reasonable approach can be used to apply the porosity, although specific approaches may be desirable with respect to the nature of the material, convenience of processing and the characteristics of the resulting pores. Specifically, the shape and size of the pores may depend on the processing approach. Many processing approaches produce randomly positioned pores, while other approaches produce an ordered array of pores.

For any of the preferred materials, some form of etching can be performed to introduce the desired porosity. A mask can be used to shield selected portions of the substrate such that the pores are formed at the unshielded locations. Masking technology is well established in the semiconductor field. This technology can be adapted to the pore formation described herein. The selected etching approach generally depends on the particular material and on the nature of the desired pores. Suitable etching approaches can involve, for example, ions, electrons, or reactive vapors. Etching with an ion beam or an electron beam is generally performed in a vacuum chamber. The energy of the particles, the beam density and the etching time can be selected to achieve the desired pore characteristics for the particular material, which can be, for example, metal, ceramic, carbonaceous solids or polymer. Pore formation with photolithography using a mask is described in U.S. Pat. No. 5,651,900 to Keller et al., entitled "Microfabricated Particle Filter," incorporated herein by reference.

Generally, the pores can also be introduced by mechanically striking the surface of the rigid material. For example, for pores that are not excessively small, a fine point can be pressed against the surface either in a pattern or randomly to generate the pores. The point should have a hardness comparable to or greater than the surface material. Similarly, the pores can be introduced by sand blasting the surface. In sand blasting, appropriate size particles or a particle dispersion in a liquid is projected at the surface with sufficient force to form the pores. Appropriate equipment for the sand blasting is commercially available.

Similarly, the pores can be introduced by micromachining the surface. Micromachining involves a focused beam that generally is used to form an ordered array of pores, although a random distribution can be approximated, if desired. For example, micro-electro-discharge micromaching, laser-beam micromachining or electron beam micromachining can be used to generate the pores. Micromachining technology can be used to perform extremely precise machining with tolerances presently as low as 50 to 100 nanometer. Micromachining for pore formation generally is described in U.S. Pat. No. 5,256,360 to Li, entitled "Method Of Manufacturing A Precision Micro-Filter," incorporated herein by reference.

Alternatively, a chemical process can be used to form the pores. For example, a soluble composition can be incorporated into the rigid material. This approach is particularly suitable for polymer materials. The polymer article can be formed, for example, using various melt casting or solvent casting approaches. If the article is formed with solvent casting, the particles can be selected to be insoluble in the solvent used to form the polymer material but soluble in another solvent used to remove the particles and form the pores. For example, many polymers can be processed in non-polar organic solvents, while many metal salts, such as ferric chloride ($FeCl_3$), are soluble in water and insoluble in non-polar organic solvents. Thus, particles of ferric chloride can be mixed with the polymer during processing in a non-polar organic solvent. Following the formation of the article, the accessible ferric chloride is removed by soaking the article in water.

Similarly, powders that decompose upon heating can be incorporated into the material. For example, ammonium bicarbonate ($NH_4HCO_3$) decomposes into ammonia ($NH_3$), carbon dioxide ($CO_2$) and water vapor ($H_2O$) upon heating above 60° C. Thus, ammonium bicarbonate powder can be incorporated into, for example, a polymer. Upon subsequent heating above 60° C., the ammonium bicarbonate decomposes to leave pores. The material should be selected such that it is not damaged by heating to the decomposition temperature of the pore former. Heating to a temperature just above 60° C. would be appropriate for many of the materials of interest.

The nature of the pores formed from removing chemical powder depends on the size and quantity of powders included. If the powders are removed with a solvent, a porous network can result if the solvent can reach the powders embedded throughout the material. If a high enough density of powders is used, proximity of adjacent powder particles results in the formation of a porous network. Alternatively, if a lower density of powders is used, the solvent may not be able to penetrate into the article to dissolve completely embedded particles. Generally, for any solid pore forming agent, the composition prior to activating the pore forming agent includes a selected amount to yield the desired level of porosity. For embodiments in which in vivo colonization of the material is desired, the porous material can have a porosity from about 1 volume percent to about 40 volume percent, in many embodiments from about 3 volume percent to about 25 volume percent and in other embodiments from about 10 volume percent to about 20 volume percent. For embodiments in which in vitro colonization of the material is desired, the porous material generally has a porosity of at least about 40 volume percent, in other embodiments from about 45 volume percent to about 70 volume percent and in further embodiments from about 50 volume percent to about 65 volume percent.

For some materials, especially for polymers, pores can be formed by introducing gas bubbles into the material during processing. For example, a melt processed polymer can be agitated or bubbled with gas to induce bubble formation. The polymer can be cooled under conditions to retain the bubbles in the structure. Similarly, for polymer formation using a solvent process or a melt process, a foaming agent can be introduced to create bubbles. Selection of a suitable foaming agent may depend on the composition of the polymer and the processing approach. Suitable foaming agents are known in the polymer field and are available commercially.

Specifically, foaming agents include volatile liquids that form gas during the processing. Volatile liquids include, for example, n-pentane, 2,2-dimethylpropane, 1-pentene, n-hexane, 2-methylpentane, 3-methylpentane, 2,2-dimethylbutane, cyclohexane, n-heptane, 2,2-dimethylpentane, 2,4-dimethylpentane, 3-ethylpentane, 1-heptene, toluene, trichloromethane, tetrachloromethane, trichlorofluoromethane, methanol, 2-propanol, isopropyl ether, methyl ethyl ketone, and the like. Other foaming agents include FLUORINERT® liquids from 3M Specialty Chemicals, West Caldwell, N.J., USA, FREON® and Vetrel® fluoronated solvents from DuPont, Wilmington, Del., USA and GALDEN® perfluorinated polyethers from Ausimont, USA. Other foaming agents decompose upon heating, such as azides that release nitrogen gas and sodium bicarbonate that releases carbon dioxide gas upon acidification. The amount of foaming agent used generally depends on the desired pore density. The foaming agent during processing generally is included at concentrations from about 0.1 weight percent to about 40 weight percent and for most embodiments from about 1 weight percent to about 20 weight percent.

Cell Colonization

The porous material is suitable for in vivo or in vitro affiliation of cells with the material. In vivo affiliation of cells with the porous material has the simplicity that cell cultures do not have to be maintained. Avoidance of a cell culture simplifies the process and reduces costs while generating the desired results under natural conditions such that the colonization process generates a stable cell population. However, in vitro cell colonization provides more control over the cell colonization process. In addition, with in vitro cell colonization, the advantages resulting from the presence of cells within the pores is obtained as soon as the medical device is contacted with the patient's fluids.

To accomplish in vivo affiliation of cells with the porous material, the medical device with the porous material is contacted with the patient's body fluids, generally by implanting the device into the patient. With the pores facilitating cell colonization, the porous material and/or adjacent areas are suitable seeding ground for cell colonization by cells that are circulating in the patient's fluids. Thus, circulating cells or nearby cells of the patient affiliate with the material and can form a surface layer of viable tissue material on top of the rigid material. Since natural processes are relied upon to effectuate the cell colonization process, appropriate cells are associated with the material upon implantation. Also, the cells inherently adapt to the conditions surrounding the device, such as shear forces from the flow. Thus, the cells may generate adhesion compounds or other useful compounds and/or exhibit a desirable morphology to facilitate their colonization process.

The in vitro affiliation of cells with the porous material can be accomplished in a cell culture system. In order to reduce the possibility of transplant rejection, the mammalian cells used for in vitro colonization preferably are autologous cells, i.e., cells from the ultimate recipient. In vitro affiliation of cells with the material can be performed at hospitals where the patient's cells can be removed for use in a cell culture system. Alternatively, cells from another donor can be used for in vitro colonization. If cells from another donor are used, generally the cells are selected using accepted blood factors for establishing an acceptable level of compatibility to reduce complications from rejection.

Preferred cell types include progenator cells, endothelial cells, fibroblast cells and combinations thereof. Association of endothelial cells is particularly appropriate in the production of prostheses that replace structures that naturally have an endothelial or epithelial cell lining, such as vascular components, cardiovascular structures, portions of the lymphatic system, uterine tissue or retinal tissue. Fibroblasts are collagen secreting cells that maintain the extracellular matrix. They are capable of a variety of different functions depending on their association with a specific tissue. Myofibroblasts are fibroblasts that express relatively more contractile proteins such as myosin and actin. In situ, fibroblasts reside below an endothelial monolayer that covers the surface of vascular tissue.

The cells can be harvested from the patient's blood or bone marrow. Alternatively, suitable cells could be harvested from, for example, adipose tissue of the patient. The harvesting process can involve liposuction followed by collagenase digestion and purification of microvessel endothelial cells. A suitable process is described further in S. K. Williams, "Endothelial Cell Transplantation," Cell Transplantation 4:401-410 (1995), incorporated herein by reference and in U.S. Pat. No. 4,883,755, entitled "Method Of Reendothelializing Vascular Linings," U.S. Pat. No. 5,372,945, entitled "Device And Method For Collecting And Processing Fat Tissue And Procuring Microvessel Endothelial Cells To Produce Endothelial Cells To Produce Endothelial Cell Product," and U.S. Pat. No. 5,628,781, entitled Implant Materials, Methods Of Treating The Surface Of Implants With Microvascular Endothelial Cells, And The Treated Implants Themselves," all three incorporated herein by reference.

Purified endothelial cells can be suspended in an appropriate growth media such as M199E (e.g., Sigma Cell Culture, St. Louis, Mo.) with the addition of autologous serum. Other cell types can be suspended similarly. The porous materials can be incubated in a stirred cell suspension for a period of hours to days to allow for cell seeding. Cell seeding provides random attachment of cells that can proliferate to coat the surface of the prosthetic substrate either before or after implantation into the patient. Alternatively, the prosthetic substrate can be incubated under a pressure gradient for a period of minutes to promote cell sodding. A suitable method for cell sodding can be adapted from a procedure described for vascular grafts in the S. K. Williams article, supra.

In addition, the prosthetic substrate can be placed in a culture system where the patient's endothelial cells are allowed to migrate onto the surface of the prosthetic substrate from adjacent tissue culture surfaces. If either attachment or migration of endothelial cells is performed under conditions involving physiological shear stress, then the endothelial cells colonizing the surface of the substrate may express appropriate adhesion proteins that allow the cells to adhere more tenaciously following implantation.

Thus, by contacting harvested cells with the porous material in a cell culture system, the cells are associated with the material. A pool of viable cells is formed within the pores based on cells from the patient or other donor prior to implantation. The cells modify the surface of the porous material such that the flow over the material is immediately modified upon implantation. However, the cells require suitable conditions to maintain their viability between colonization of the surface and implantation.

Assembly, Storage, Shipping and Use

If the medical device includes a plurality of components, the porosity preferably is introduced to the material surface prior to the assembly of the components into the resulting device. However, if the additional components do not interfere with the process for forming the pores, the pores can be formed following the integration of the components or a portion of the components into the final device. As noted above, preferred devices include mechanical heart valve prostheses. For heart valve embodiments, all surfaces of the rigid occluder are preferably treated to form pores. In addition, the internal surfaces of the valve ring that contact the blood flow are also preferably treated to form pores. The occluder and other components can be treated to form porosity and then assembled into the heart valve prosthesis.

Similarly, any pore filling matrix, either hydrogel and/or structural protein, and/or bioactive agents generally are placed within the pores prior to assembly of the components, although it may be possible to apply the pore filling materials and/or the bioactive agent following assembly. If the material includes hydrogels, structural proteins and/or bioactive agents, the subsequent handling of the material may require additional considerations. For example, some hydrogels, structural proteins and bioactive agents must remain hydrated to prevent irreversible degradation of the compositions. In these embodiments, the materials must be stored in solution or in a moist atmosphere.

If the medical devices are distributed without associated cells, the medical devices can be stored appropriately. Preferred storage techniques minimize the risk of microbial contamination. For example, if the medical device must be kept moist, the medical device can be stored in a sealed container with sterile buffer and/or saline solution. Containers for the storage of medical devices in a moist environment without immersing the device are described, for example, in U.S. Pat. No. 5,960,956 to Langanki et al., entitled "Storage Container," incorporated herein by reference.

In a sealed container the device is not subjected to a continuous supply of fluids. Nevertheless, consideration should be given to possible loss during storage of any bioactive agents, hydrogels and/or structural proteins from the device or loss during storage of activity of any bioactive agents. If excessive loss of constituents is a possibility, the storage time can be limited appropriately to keep the loss to an acceptable level.

The containers generally are packaged with instructions for the use of the medical devices along with desired and/or required labels. The containers are distributed to health care professionals for surgical implantation of the prostheses or other uses of the medical devices. The implantation is performed by a qualified health care professional. The surgical implantation generally involves the replacement of damaged tissue with the prosthesis or the implantation of a catheter or the like to provide suitable access into the patient.

As noted above, in vitro affiliation of cells with a medical device with porosity preferably is performed at hospitals where the patient's cells can be removed for use in a cell culture system. The harvested cells can be contacted with the device or components thereof in a cell culture system to associate the cells with the porous material. Thus, a cell colonized surface is formed based on cells from the patient prior to implantation. The cell colonized material can be stored in the cell culture system prior to implantation. If the colonization of the medical device with cells is performed remotely with the patient's cell or cells from another donor, the medical devices generally are packaged carefully and shipped quickly for use shortly after shipping such that the cells remain viable at implantation.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What we claim is:

1. An implantable prosthesis comprising:
   at least one occluder, wherein the at least one occluder comprises a rigid material with pores formed in the rigid material, wherein the rigid material is selected from the group consisting of metals, carbonaceous solids, polymers, and ceramics; and
   a filler comprising a hydrogel or a structural protein or a bioactive agent or mixtures thereof, the filler being located within the pores, wherein said rigid porous material with the filler presents a smoother surface for fluid flow than pores without filler and wherein the filler prevents back flow of fluid through the pores of the occluder.

2. The implantable prosthesis of claim 1 wherein the filler fills the pores.

3. The implantable prosthesis of claim 2 wherein the rigid porous material with the filler presents a smooth surface to flow.

4. The implantable prosthesis of claim 1 wherein the filler partly fills the pores.

5. The implantable prosthesis of claim 1 wherein the filler comprises a hydrogel selected from the group consisting of poly(ethylene glycol), poly(hydroxyethyl methacrylate), partially or fully hydrolyzed poly(vinyl alcohol), poly(vinylpyrrolidone), poly(ethyloxazoline), poly(ethylene oxide)-co-poly(propylene oxide) block copolymers, polyamines, polyacrylamide, hydroxypropylmethacrylate, carboxymethyl cellulose, hydroxyethyl cellulose, methylhydroxypropyl cellulose, polysucrose, hyaluronic acid, alginate, chitosan, dextran, gelatin and mixtures and copolymers thereof.

6. The implantable prosthesis of claim 1 wherein the filler comprises a structural protein.

7. The implantable prosthesis of claim 6 wherein the structural protein is an extracellular matrix protein.

8. The implantable prosthesis of claim 1 wherein the filler comprises a mixture of hydrogel and structural protein.

9. The implantable prosthesis of claim 1 wherein the filler comprises a biologically active agent.

10. The implantable prosthesis of claim 9 wherein the biologically active agent is dispersed within the hydrogel or protein.

11. The implantable prosthesis of claim 9 wherein the biologically active agent is selected from the group consisting of a growth factor, a cell attraction compound, an anticoagulant and combinations thereof.

12. The implantable prosthesis of claim 9 wherein the biologically active agent is VEGF.

13. The implantable prosthesis of claim 9 wherein the bioactive agent is a growth factor.

14. The implantable prosthesis of claim 9 wherein the bioactive agent is a progenitor attraction compound.

15. The implantable prosthesis of claim 9 wherein the bioactive agent is an anticoagulant.

16. The implantable prosthesis of claim 1 wherein the pores have an interconnecting porosity.

17. The implantable prosthesis of claim 1 wherein a nutrient is also located within the pores.

18. The implantable prosthesis of claim 1 further comprising viable cells.

19. The implantable prosthesis of claim 1 wherein the prosthesis is a mechanical heart valve prosthesis comprising an orifice ring and the at least one occluder attached to the orifice ring.

20. The implantable prosthesis of claim 1 wherein the rigid polymer is selected from the group consisting of polysulfones, polyacetals, polyethersulfones, polyarylsulfones, polyetheretherketones, polyamides, polyurethanes, polytetrafluoroethylene, other fluoronated and perfluoronated vinylpolymers, polycarbonate, polyetherimides, tyrosine-derived polyarylate polymers, polylactic acid and polyglycolic acid-based composites and copolymers and mixtures thereof.

21. The implantable prosthesis of claim 1 and wherein the occluder comprises an upstream side and a downstream side and wherein the occluder comprises a network of interconnected pores that provide a passageway for the fluid from the downstream side to the upstream side and wherein the filler is placed within the pores to prevent the backflow of fluid from the downstream side to the upstream side of the occluder.

22. An implantable medical device comprising;
   at least one occluder, wherein the at least one occluder comprises a rigid material having pores formed in the rigid material and present substantially close to a surface of the rigid material, wherein the rigid material is selected from the group consisting of metals, carbonaceous solids, polymers, and ceramics; and a filler, said filler comprising a hydrogel or a structural protein or a bioactive agent or mixtures thereof, the filler being located within the pores to promote cellular attachment and proliferation and wherein the filler prevents back flow of fluid through the pores of the occluder.

23. The medical device of claim 22 wherein said device is for contacting bodily fluids and/or tissue after implantation.

24. The medical device of claim 22 wherein said filler fills the pores.

25. The medical device of claim 24 wherein said rigid porous material with the filler presents a smooth surface to flow.

26. The medical device of claim 22 wherein said bioactive agent is dispersed within the hydrogel or protein.

27. The medical device of claim 22 wherein the bioactive agent is selected from the group consisting of a growth factor, a cell attraction compound, an anticoagulant and combinations thereof.

28. The medical device of claim 22 wherein the bioactive agent is VEGF.

29. The medical device of claim 22 wherein the bioactive agent is a progenitor attraction compound.

30. The medical device of claim 22 wherein the bioactive agent is an anticoagulant.

31. An implantable medical device comprising;
at least one occluder, wherein the at least one occluder comprises a rigid material having pores substantially extending through the rigid material to form a porous network, wherein the rigid material is selected from the group consisting of metals, carbonaceous solids, polymers, and ceramics; and
a filler, said filler comprising a hydrogel or a structural protein or a bioactive agent or mixtures thereof, the filler being located within the pores, and said porous network does not provide significant blood flow through the porous material and wherein the filler prevents back flow of fluid through the pores of the occluder.

32. The medical device of claim 31 wherein said porous network promotes cellular attachment and proliferation.

33. The medical device of claim 31 wherein said filler fills the pores.

34. The medical device of claim 33 wherein said rigid porous material with the filler presents a smooth surface to flow.

35. The medical device of claim 31 wherein said bioactive agent is dispersed within the hydrogel or protein.

36. The medical device of claim 31 wherein the bioactive agent is selected from the group consisting of a growth factor, a cell attraction compound, an anticoagulant and combinations thereof.

37. The medical device of claim 31 wherein the bioactive agent is VEGF.

* * * * *